(12) United States Patent
Koester

(10) Patent No.: US 8,386,047 B2
(45) Date of Patent: Feb. 26, 2013

(54) IMPLANTABLE HERMETIC FEEDTHROUGH

(75) Inventor: Kurt J. Koester, Los Angeles, CA (US)

(73) Assignee: Advanced Bionics, Valencia, CA (US)

( * ) Notice: Subject to any disclaimer, the term of this patent is extended or adjusted under 35 U.S.C. 154(b) by 126 days.

(21) Appl. No.: 12/836,899

(22) Filed: Jul. 15, 2010

(65) Prior Publication Data
US 2012/0016444 A1    Jan. 19, 2012

(51) Int. Cl.
*A61N 1/00* (2006.01)
(52) U.S. Cl. .................................................... 607/57
(58) Field of Classification Search ............... 607/57, 607/36, 37; 174/152 GM; 29/831; 340/10.1
See application file for complete search history.

(56) References Cited

U.S. PATENT DOCUMENTS

| 4,445,511 A * | 5/1984 | Cowdery et al. ............ 607/37 |
| 4,700,881 A | 10/1987 | Ryan |
| 4,721,831 A | 1/1988 | Vora |
| 4,785,827 A | 11/1988 | Fischer |
| 4,837,230 A | 6/1989 | Chen et al. |
| 4,874,910 A | 10/1989 | McCoy |
| 5,085,720 A | 2/1992 | Mikeska et al. |
| 5,254,191 A | 10/1993 | Mikeska et al. |
| 5,282,841 A * | 2/1994 | Szyszkowski ............... 607/36 |
| 5,304,517 A | 4/1994 | Casey et al. |
| 5,315,239 A | 5/1994 | Vitriol |
| 5,333,095 A | 7/1994 | Stevenson et al. |
| 5,336,246 A | 8/1994 | Dantanarayana |
| 5,440,802 A | 8/1995 | Whitney et al. |
| 5,474,741 A | 12/1995 | Mikeska et al. |
| 5,474,834 A | 12/1995 | Tanahashi et al. |
| 5,513,793 A | 5/1996 | Malmgren |
| 5,591,287 A | 1/1997 | Clegg et al. |
| 5,620,476 A * | 4/1997 | Truex et al. .................. 607/36 |
| 5,683,435 A | 11/1997 | Truex et al. |
| 5,738,270 A | 4/1998 | Malmgren |
| 5,750,926 A | 5/1998 | Schulman et al. |
| 5,855,995 A | 1/1999 | Haq et al. |
| 5,937,321 A | 8/1999 | Beck et al. |
| 6,008,980 A | 12/1999 | Stevenson et al. |
| 6,041,496 A | 3/2000 | Haq et al. |
| 6,139,666 A | 10/2000 | Fasano et al. |
| 6,146,743 A | 11/2000 | Haq et al. |

(Continued)

FOREIGN PATENT DOCUMENTS

EP    0660449 A2    6/1995
EP    0660449 A3    6/1995

(Continued)

OTHER PUBLICATIONS

Koester et al.; Electrical Feedthrough Assembly; U.S. Appl. No. 12/836,831, filed Jul. 15, 2010.

(Continued)

*Primary Examiner* — George Manuel
*Assistant Examiner* — Robert N Wieland
(74) *Attorney, Agent, or Firm* — Steven L. Nichols; Van Cott, Bagley, Cornwall & McCarthy P.C.

(57) ABSTRACT

An implantable hermetic system includes a hermetic case and a hermetic feedthrough sealed into an aperture in the case. The hermetic feedthrough includes vias which form electrically conductive paths through the hermetic feedthrough. A header that includes integral interconnection contacts is attached to the case. The vias are electrically joined to the interconnection contacts.

24 Claims, 14 Drawing Sheets

U.S. PATENT DOCUMENTS

| | | |
|---|---|---|
| 6,205,032 B1 | 3/2001 | Shepherd |
| 6,284,080 B1 | 9/2001 | Haq et al. |
| 6,414,835 B1 | 7/2002 | Wolf et al. |
| 6,516,808 B2 | 2/2003 | Schulman |
| 6,548,011 B1 | 4/2003 | Rhee et al. |
| 6,554,178 B1 | 4/2003 | Tsukamoto |
| 6,560,860 B2 | 5/2003 | Shepherd |
| 6,660,116 B2 | 12/2003 | Wolf et al. |
| 6,863,450 B2 | 3/2005 | Mazotti et al. |
| 6,989,200 B2 | 1/2006 | Byers et al. |
| 7,068,491 B1 | 6/2006 | Burdon et al. |
| 7,073,961 B2 | 7/2006 | Mazotti et al. |
| 7,127,286 B2 | 10/2006 | Mech et al. |
| 7,142,909 B2 | 11/2006 | Greenberg et al. |
| 7,164,572 B1 | 1/2007 | Burdon et al. |
| 7,174,223 B2 | 2/2007 | Dalton et al. |
| 7,190,051 B2 | 3/2007 | Mech et al. |
| 7,211,103 B2 | 5/2007 | Greenberg et al. |
| 7,211,510 B2 | 5/2007 | Meadows |
| 7,257,446 B2 | 8/2007 | Greenberg et al. |
| 7,291,540 B2 | 11/2007 | Mech et al. |
| 7,341,802 B1 | 3/2008 | Ota et al. |
| 7,480,988 B2 | 1/2009 | Ok et al. |
| 7,497,846 B2 | 3/2009 | Uhland et al. |
| 7,524,535 B2 | 4/2009 | Kim et al. |
| 7,818,876 B2 | 10/2010 | Suaning |
| 7,901,761 B1 | 3/2011 | Jiang et al. |
| 7,988,507 B2 | 8/2011 | Darley et al. |
| 7,996,982 B2 | 8/2011 | Darley et al. |
| 2002/0139556 A1 | 10/2002 | Ok et al. |
| 2003/0109903 A1 | 6/2003 | Berrang et al. |
| 2004/0093038 A1 | 5/2004 | Biggs et al. |
| 2005/0247475 A1* | 11/2005 | Stevenson et al. ......... 174/50.51 |
| 2005/0288733 A1 | 12/2005 | Greenberg et al. |
| 2006/0186473 A1 | 8/2006 | Mech et al. |
| 2006/0283624 A1 | 12/2006 | Ok et al. |
| 2007/0005112 A1 | 1/2007 | Greenberg et al. |
| 2007/0021787 A1 | 1/2007 | Greenberg et al. |
| 2007/0041164 A1 | 2/2007 | Greenberg et al. |
| 2007/0060969 A1 | 3/2007 | Burdon et al. |
| 2007/0060970 A1* | 3/2007 | Burdon et al. .................. 607/37 |
| 2007/0096281 A1 | 5/2007 | Greenberg et al. |
| 2007/0112396 A1 | 5/2007 | Dalton et al. |
| 2007/0207569 A1 | 9/2007 | Greenberg et al. |
| 2007/0236861 A1 | 10/2007 | Burdon et al. |
| 2007/0277374 A1 | 12/2007 | Suaning |
| 2008/0027515 A1* | 1/2008 | Harris et al. ..................... 607/62 |
| 2008/0046021 A1 | 2/2008 | Greenberg et al. |
| 2008/0053638 A1* | 3/2008 | Appleby et al. .............. 164/129 |
| 2008/0060834 A1 | 3/2008 | Eck et al. |
| 2008/0077195 A1 | 3/2008 | Greenberg et al. |
| 2008/0208289 A1 | 8/2008 | Darley et al. |
| 2008/0209723 A1 | 9/2008 | Darley et al. |
| 2008/0217784 A1 | 9/2008 | Binder et al. |
| 2009/0034769 A1 | 2/2009 | Darley et al. |
| 2009/0124965 A1 | 5/2009 | Greenberg et al. |
| 2010/0019985 A1 | 1/2010 | Bashyam et al. |
| 2010/0292760 A1 | 11/2010 | Leigh et al. |
| 2011/0000699 A1* | 1/2011 | Bealka et al. ................. 174/151 |
| 2011/0139484 A1 | 6/2011 | Koester et al. |
| 2012/0012374 A1 | 1/2012 | Koester et al. |

FOREIGN PATENT DOCUMENTS

| | | |
|---|---|---|
| EP | 0441528 B1 | 10/1996 |
| EP | 0844899 B1 | 7/2003 |
| EP | 1547207 B1 | 8/2011 |
| GB | 2134335 | 8/1984 |
| JP | 59111868 A2 | 6/1984 |
| JP | 60211345 A2 | 4/1985 |
| JP | 61145526 | 7/1986 |
| JP | 6356378 A2 | 6/1988 |
| JP | 63156378 A2 | 6/1988 |
| JP | 01/294061 | 11/1989 |
| JP | 04023303 A2 | 1/1992 |
| JP | 06061611 A | 3/1994 |
| JP | 06218872 | 8/1994 |
| JP | 07-211851 | 8/1995 |
| JP | 09147710 A | 6/1997 |
| JP | 10126119 A2 | 5/1998 |
| JP | 10194856 A | 7/1998 |
| JP | 11224984 A | 8/1999 |
| JP | 2001-284774 | 10/2001 |
| JP | 2002368422 A2 | 12/2002 |
| JP | 2004-119587 | 4/2004 |
| JP | 2006032439 A2 | 2/2006 |
| JP | 2009246391 A2 | 10/2009 |
| WO | 89/07834 | 8/1989 |
| WO | 94/08539 | 4/1994 |
| WO | 97/06853 | 2/1997 |
| WO | 2004/030159 | 4/2004 |
| WO | 2007/070989 | 6/2007 |
| WO | 2009/003235 | 1/2009 |
| WO | 2009/009827 | 1/2009 |

OTHER PUBLICATIONS

Rodel et al; Ceramic/Metal Interfacial Crack Growth:Toughening by Controlled Microcracks and Interfacial Geometries; Acta metall. vol. 36, No. 8, pp. 2083-2093, 1988.

Adtech Ceramics, Design & Capabilities Guide, Ceramic Packages-Chemical Milling-Injection Molding, Advanced Technical Ceramics Company 2007.

Kurt J. Koester; "Electrical Feedthrough Assembly"; U.S. Appl. No. 12/836,831, filed Jul. 15, 2010.

Kurt J. Koester; "Particulate Toughened Ceramic Feedthrough"; U.S. Appl. No. 61/423,355, filed Dec. 15, 2010.

MacDonald et al, Transient Liquid Phase Bonding, Department of Materials Science and Engineering, Massachusetts Institute of Technology, Cambridge, Massachusetts 02139; vol. 22; pp. 23-46; Aug. 1, 1992.

Shalz et al, Ceramic Joining Part I Partial transient liquid-phase bonding of alumina via Cu/Pt interlayers. Journal of Materials Science 28 (1993) 1673-1684.

Shalz et al., Ceramic Joining II Partial transient liquid-phase bonding of alumina via Cu/Ni/Cu multilayer interlayers, Journal of Materials Science 29; vol. 29; pp. 3200-3208; 1994.

Shalz et al., Ceramic Joining III Bonding of alumina via Cu/Nb/Cu interlayers, Journal of Materials Science 29 (1994) vol. 29; pp. 3678-3690; 1994.

Sugar et al, Ceramic joining IV. effects of processing conditions on the properties of alumina joined via Cu/Nb/Cu interlayers, Journal of Materials Science 36 (2001) 5609-5624.

Sugar et al, Liquid-Film-Assisted Formation of Alumina/Niobium Interfaces, Journal of the American Ceramic Society, vol. 85 Issue 10, pp. 2523-2530, Published Online: May 10, 2005.

Platinum Foil in Ceramic Bonding, Platinum Metals Review, vol. 37 Jul. 1, 1993, http://www.platinummetalsreview.com/pdf/pmr-v37-i3-130-184.pdf.

* cited by examiner

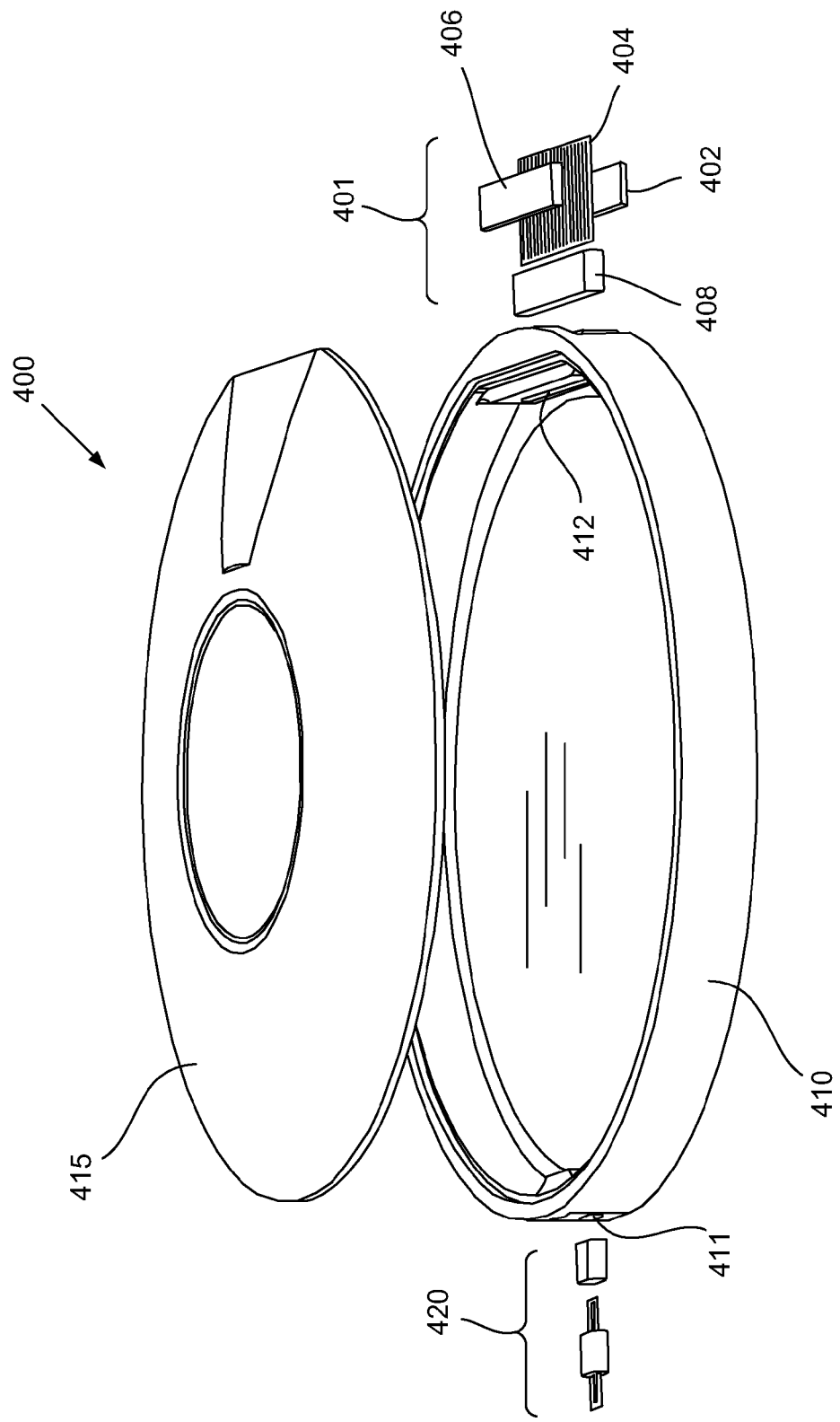

IMPLANTABLE HERMETIC FEEDTHROUGH

BACKGROUND

A variety of implanted medical devices can be used to extend and improve the life of a patient. These implanted medical devices often include electronics that monitor internal and external parameters and control the application of various therapies. To prevent body fluids from damaging electronic components that may be present within the device, the circuitry included in the internal unit is often enclosed by a hermetically sealed case. An electrical feedthrough may be used to transfer signals from the circuitry inside the hermetic case to the exterior of the case and vice versa. This electrical feedthrough maintains the integrity of the hermetic case, while allowing electrical signals to pass through.

Making reliable electrical connections between the vias in the hermetic feedthrough and an external device can be challenging. In some devices, the hermetic feedthrough and vias may be miniaturized. The miniaturization may result in very small cross-section vias, wires and connections. Tensile or compressive forces may be applied to wires or vias, resulting in stresses in the wires, vias, and connections. Implantation in a dynamic biological system may lead to fatigue failure of the connections, vias, or wires. The connections may also be degraded by biological or chemical attack.

BRIEF DESCRIPTION OF THE DRAWINGS

The accompanying drawings illustrate various embodiments of the principles described herein and are a part of the specification. The illustrated embodiments are merely examples and do not limit the scope of the claims.

FIG. 4 is an exploded view of an illustrative hermetic enclosure that houses cochlear implant electronics, according to one embodiment of principles described herein.

Throughout the drawings, identical reference numbers designate similar, but not necessarily identical, elements.

DETAILED DESCRIPTION

Figure 1:
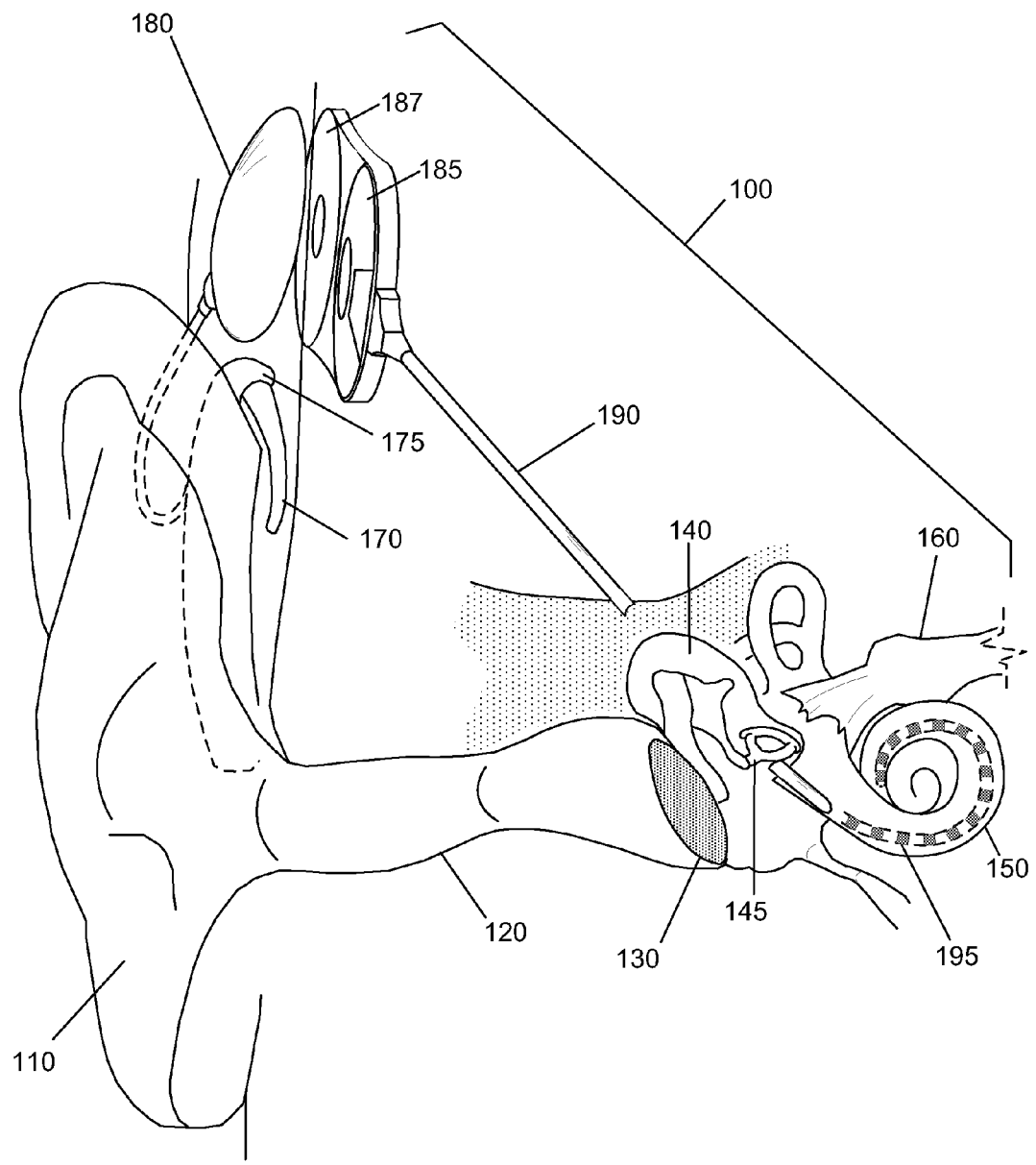
FIG. 1 is a diagram showing an illustrative cochlear implant system, according to one embodiment of principles described herein.

One example of an implanted medical device that may include a hermetic feedthrough is a cochlear prosthesis. A cochlear prosthesis may be used to restore a sense of hearing in a patient by directly stimulating nerve cells. One component of the cochlear prosthesis is a hermetically sealed processor that is typically implanted underneath the skin above the ear. The internal processor receives signals from an exterior unit and converts the signals into electrical impulses. An electrical feedthrough may be used to transfer signals from the circuitry inside the hermetic case to the exterior of the case and vice versa. The electrical impulses travel through a hermetic feedthrough and along wires that run from the processor to electrodes implanted in the cochlea.

To increase comfort and ease of implantation, as well as minimize surgical trauma, it is desirable that the cochlear implant be as small as possible. Depending on the design, reducing the size of the implant may also reduce the risk of damage to the implant from blows or impacts. However, reducing the size of the implant has the associated challenge of shrinking the size of the hermetic feedthroughs. Each hermetic feedthrough design has manufacturing and material limitations on how much it can be scaled down, i.e., there are limitations imposed by the fabrication method, structure, leak path, etc. of the feedthrough.

The present specification relates to making electrical connections with vias of a hermetic electrical feedthrough. Making reliable electrical connections between the vias in the hermetic feedthrough and an external device can be challenging. As discussed above, the hermetic feedthrough and vias may be miniaturized. This miniaturization may result in very small cross-section vias, wires, and connections. Implantation in a dynamic biological system may lead to fatigue failure of the connections, vias, or wires. Tensile or compressive forces may be applied to wires or vias, during manufacture, implantation, or throughout the life of the device, resulting in stresses in the wires, vias, and connections, which could lead to failures. The connections may be chemically attacked by biological substances. The illustrative system and method described below for making electrical connections to an implantable hermetic feedthrough mitigates these challenges and results in a robust and versatile connection.

In the following description, for purposes of explanation, numerous specific details are set forth in order to provide a thorough understanding of the present systems and methods.

It will be apparent, however, to one skilled in the art that the present apparatus, systems, and methods may be practiced without these specific details. Reference in the specification to "an embodiment," "an example," or similar language means that a particular feature, structure, or characteristic described in connection with the embodiment or example is included in at least that one embodiment, but not necessarily in other embodiments. The various instances of the phrase "in one embodiment" or similar phrases in various places in the specification are not necessarily all referring to the same embodiment.

FIG. 1 is a diagram showing one illustrative embodiment of a cochlear implant (100) that is surgically placed within the patient's auditory system. Ordinarily, sound enters the outer ear (110) and is directed into the auditory canal (120) where the sound wave vibrates the tympanic membrane (130). The motion of the tympanic membrane is amplified and transmitted through the ossicular chain (140) which consists of three bones in the middle ear. The third of the ossicles, the stapes, or stirrup, (145) contacts the outer surface of the cochlea (150) and causes movement of the fluid within the cochlea (150). Cochlear hair cells respond to the fluid-borne vibration in the cochlea (150) and trigger neural electrical signals that are conducted from the cochlea (150) to the auditory cortex by the auditory nerve (160).

As indicated above, the cochlear implant (100) is a surgically implanted electronic device that provides a sense of sound to a person who is profoundly deaf or severely hard of hearing. As also noted above, in many cases, deafness is caused by the absence or destruction of the hair cells in the cochlea, i.e., sensorineural hearing loss. In the absence of properly functioning hair cells, there is no way auditory nerve impulses can be directly generated from ambient sound. Thus, conventional hearing aids, which amplify external sound waves, provide no benefit to persons suffering from complete sensorineural hearing loss.

Unlike hearing aids, the cochlear implant (100) does not amplify sound, but works by directly stimulating the auditory nerve (160) with electrical impulses. Consequently, providing a cochlear prosthesis typically involves the implantation of electrodes into the cochlea. The cochlear prosthesis operates by direct electrical stimulation of the auditory nerve cells, bypassing the defective cochlear hair cells that normally traduce acoustic energy into electrical energy.

External components of the cochlear implant include a microphone (170), speech processor (175), and transmitter (180). The microphone (170) picks up sound from the environment and converts it into electrical impulses. The speech processor (175) selectively filters and manipulates the electrical impulses and sends the processed electrical signals through a cable to the transmitter (180). The transmitter (180) receives the processed electrical signals from the speech processor (175) and transmits them to the cochlear implant (100) by electromagnetic induction and/or by using radio frequencies.

In this example, the cochlear implant (100) includes an antenna (187) and an internal processor (185). The antenna (187) and internal processor (185) are secured beneath the user's skin, typically above and behind the external ear (110). The internal processor (185) includes electronic circuitry housed in a hermetically sealed enclosure. This electronic circuitry is connected by a hermetically sealed feedthrough to the antenna (187). The antenna (187) receives power and signals from the transmitter (180) via electromagnetic induction and/or radio frequency signals. The internal processor (185) processes the received signals and sends modified signals through a separate hermetic feedthrough to the cochlear lead (190) and electrodes (195). The electrodes (195) are inserted into the cochlea (150) and provide electrical stimulation to the auditory nerve (160).

The implant works by using the tonotopic organization of the cochlea. The cochlea is arranged tonotopically, also referred to as "frequency-to-place" mapping. The tonotopic structure of the cochlea enables human beings to hear a broad range of acoustic frequencies. The nerve cells sense progressively lower frequencies from the basal end of the cochlea to the apex. For normal hearing, the brain is presented with the electrical signals from the different regions of the cochlea and, because of the tonotopic configuration of the cochlea, is able to discern the acoustic frequencies being heard. A cochlear implant simulates with its electrode contacts along the length of the cochlea to mimic this process.

Figure 2:
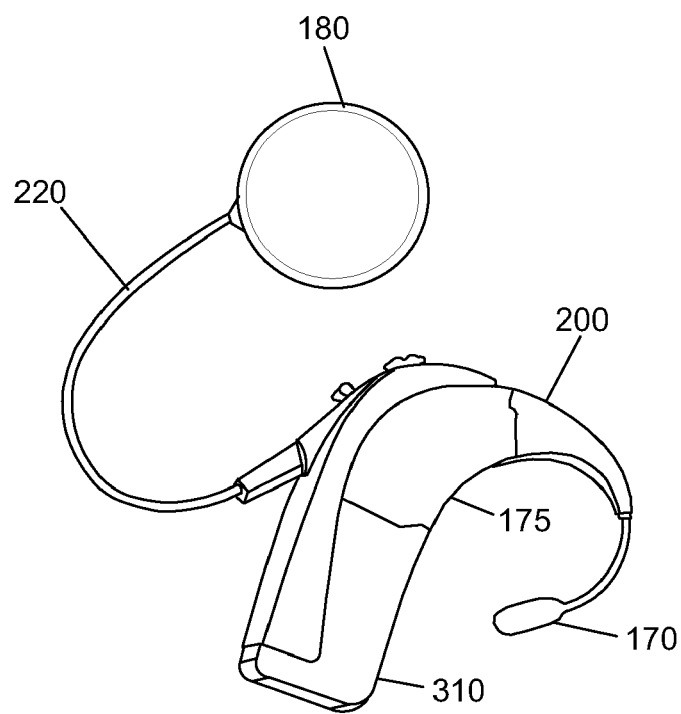
FIG. 2 is a diagram showing the external components of an illustrative cochlear implant system, according to one embodiment of principles described herein.

FIG. 2 shows one illustrative embodiment of the external components of the cochlear implant. The microphone (170) is attached to the ear hook (200). The ear hook (200) secures the external components behind the outer ear. The microphone (170) senses environmental sounds and converts those sounds into electrical impulses. The processor (175) filters and manipulates the electrical impulses it receives from the microphone (170) and transmits processed electrical sound signals along the external cable (220) to the transmitter (180). The processor (175), microphone (170) and transmitter (180) are powered by a battery (310).

Figure 3:
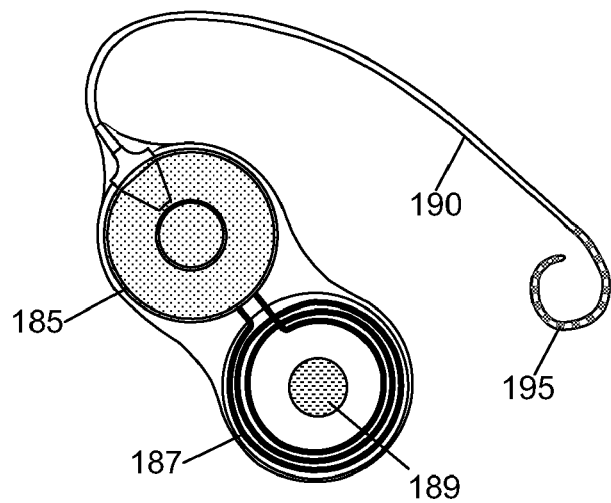
FIG. 3 is a diagram showing implanted components of an illustrative cochlear implant system, according to one embodiment of principles described herein.

FIG. 3 shows one illustrative embodiment of the internal components of the cochlear implant device. As described above, the antenna (187) is connected to the internal processor (185). According to one embodiment, the antenna (187) is a coiled wire or wires that are encapsulated by a silicone overmold. A cavity within the center portion of the antenna (187) is adapted to receive a magnet (189). The transmitter (180, FIG. 2) is held in place externally over the antenna (187) by magnetic interaction between components within the transmitter (180, FIG. 2) and the implanted antenna magnet (189). The internal processor (185) is electrically connected to antenna (187) and receives signals and power via the antenna (187). The internal processor (185) is connected to the cochlear lead (190) that terminates in a flexible end that contains the electrodes (195). The electrodes (195) consist of a plurality of individual electrode contacts made from platinum or a similar inert conductive material. These electrodes and associated wires are supported and connected by a flexible and durable biocompatible material, typically silicone rubber.

FIG. 4 is an exploded view of an illustrative hermetic enclosure (400) that houses cochlear implant electronics (not shown). In this particular embodiment, the hermetic enclosure (400) includes a case (410) and a case top (415). The case (410) and the case top (415) may be formed from a variety of biocompatible materials. According to one illustrative embodiment, the case (410) and the case top (415) are formed from titanium. The case (410) shown in FIG. 4A is a cylinder with a closed bottom and open top that is machined from a single piece of titanium. The case (410) includes two apertures (411, 412) in the radial wall that are configured to receive hermetic electrical feedthroughs (401, 420). The case top (415) is also made from titanium and can be laser welded onto a groove in the case (410). Once the case top (415) and hermetic electrical feedthroughs (401, 420) are in place, the hermetic enclosure (400) prevents liquids or gasses from entering the interior of the enclosure (400). As discussed above this prevents damage to electronics or other devices that are housed in the interior of the hermetic enclosure (400).

According to one illustrative embodiment, the electrical hermetic feedthroughs (401, 420) are formed from a set of ribbon vias (404) that are sandwiched between a top ceramic layer (406) and a bottom ceramic layer (402). As discussed below, the top ceramic layer (406) and the bottom ceramic layer (402) are joined to form a monolithic ceramic body. The ribbon vias (404) pass through the monolithic ceramic body and are sealed in the ceramic body. The ceramic body is then joined to the aperture in the case (410). In this illustrative embodiment, a braze joint (408) is illustrated as joining the ceramic body to the case (410).

In this illustrative embodiment, the hermetic feedthroughs (401, 420) are on the perimeter of the case (410). The example shown in FIG. 4, the larger hermetic feedthrough (401) provides electrical connections between the electrodes in the cochlear lead and the internal electronics that are housed in the case. The smaller hermetic feedthrough (420) makes electrical connections between the antenna and the internal electronics. The hermetic feedthroughs (401, 420) are well protected by the case (410), which may reduce likelihood that the feedthroughs would be damaged by impact loading. Locating the feedthroughs around the perimeter of the case (410) can have a number of advantages, including a reduction in the overall height of the implanted device, simplifying manufacturing, and increased design flexibility in creating connectorized electrical interfaces between the internal electronics and the cochlear electrode. According to one illustrative embodiment, the overall height of the hermetic feedthrough (401) may be less than 2 mm. For example, the height of the hermetic feedthrough may on the order of 1 mm.

However, the hermetic feedthroughs (401,420) could also be in other locations on the case (410) or the case top (415). Further, the number and size of hermetic feedthroughs (401, 420) could be varied according to the design requirements. For example, a single feedthrough could be used for all electrical connections to the internal electronics.

Figure 5A:
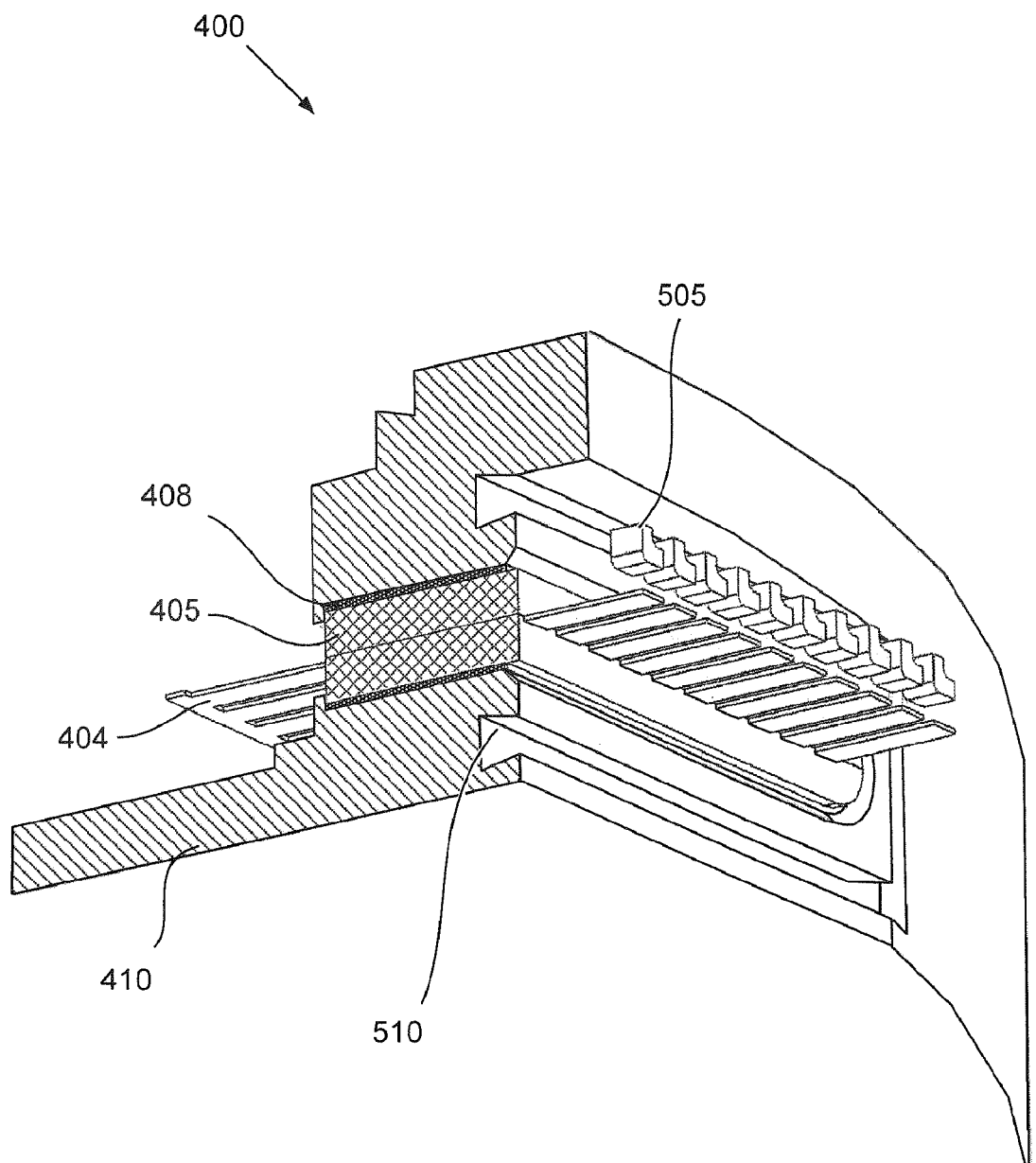
FIG. 5A is a cross sectional diagram of an illustrative hermetic case that includes a hermetic electrical feedthrough, according to one embodiment of principles described herein.

FIG. 5A is a partially cut away perspective view of the hermetic enclosure (400) shown in FIG. 4. The ribbon vias (404) extend through the ceramic body (405). The ceramic body (405) in turn is joined to the case (410) by a braze joint (408). An illustrative method for encapsulating the ribbon vias (404) in the ceramic body (405) and joining the ceramic body (405) to the case (410) using a braze joint (408) is described in U.S. application Ser. No. 12/836,831, entitled "Electrical Feedthrough Assembly," to Kurt Koester, filed Jul. 15, 2010, which is incorporated herein by reference in its entirety.

FIG. 5A shows ribbon vias (404) passing through the ceramic body (405) and extending from both sides of the ceramic body (405). The braze joint (408) seals the ceramic body (405) to the case (410). The case (410) may be formed from any biocompatible material that has the desired impermeability and mechanical characteristics. For example, titanium may be used to form the case (410). Titanium has a number of desirable characteristics, including high strength, resiliency, biocompatibility, low density, and low moisture permeability.

The ceramic body (405) may be formed from a variety of materials. For example, the ceramic body (405) may be formed from alumina. The ceramic body (405) can be joined to the case in a number of ways, including brazing, active metal brazing, ceramic/glass/metal joining, transient liquid phase bonding, or other suitable techniques. According to one illustrative embodiment, a gold or gold alloy braze material is used to form a braze joint (408) that hermetically seals the feedthrough (401) into the case (410).

The ribbon vias (404) may also be formed from a range of materials that have the desired characteristics. For example, the ribbon vias (404) may be formed from platinum. Platinum has a number of desirable characteristics, including a relatively low electrical resistance, corrosion resistance, biocompatibility, and ability to be alloyed with a number of other elements. As used in the specification and appended claims, the term "ribbon vias" refers to vias that have a width that is substantially greater than the thickness of the via. According to one illustrative embodiment, the ribbon vias (404) may be formed by micromachining a sheet of platinum foil to form a number of discretized vias. This micromachining can be performed in a variety of ways, including short pulse laser machining. The foil may have a thickness that is less than about 50 microns. The individual ribbons may have a variety of widths and geometries. In one illustrative embodiment, the platinum foil has a thickness between 25-30 microns and a width between about 120 microns and 300 microns. These ribbon vias (404) may have a number of advantages over vias that are created using platinum/glass inks, including lower resistivity. The lower electrical resistances of the ribbon vias (404) can significantly increase the power efficiency and battery life of a cochlear implant or other device.

According to one illustrative embodiment, the ceramic body (405) is formed by laying out a first segment of green ceramic tape, placing the ribbon vias (404) on the green ceramic tape, and then placing another green ceramic tape over the ribbon vias (404). This sandwiches the ribbon vias (404) between the two green ceramic tapes. The green ceramic tapes are then pressed together and sintered into the monolithic ceramic body (405) with the ribbon vias (404) embedded in the ceramic body (405) and extending out both sides of the ceramic body (405). The extension of the ribbon vias out of the ceramic body (405) can facilitate making electrical connections through the feedthrough.

As described in the reference incorporated above, the interface between the ribbon vias (404) and the ceramic body (405) may be sealed using a partial transient liquid phase technique. In the partial transient liquid phase technique, at least a portion of the platinum ribbon vias (404) may be coated with niobium. After sintering the ceramic body (405), the hermetic feedthrough (401, FIG. 4) is heated above a eutectic point. The outer portion of the ribbon vias (404) at a eutectic point melts and fills the voids surrounding the plurality of ribbon vias (404). The niobium then continues to diffuse into the center of the platinum ribbon, leaving a solid solution of niobium and platinum in the voids. This provides a seal between the ribbon vias (404) and the surrounding ceramic body (405) and decreases the permeability of the feedthrough.

FIG. 5A also shows several illustrative features which facilitate the connection of ribbon vias (404) to internal and external electrical components. According to one illustrative embodiment, the case (410) contains several dovetail grooves (510). These dovetail grooves (510) can serve to anchor a header (shown in FIG. 5B) that supports the interconnection contacts (505). As described below, the ribbon vias (404) extend out both sides of the ceramic body (405). The portions of the ribbon vias (404) that extend out of the exterior side of the ceramic body (405) are attached to the interconnection contacts (505) (as shown in FIG. 5C). The header attaches to the case by being molded or otherwise attached to dovetail grooves (510).

Figure 5B:
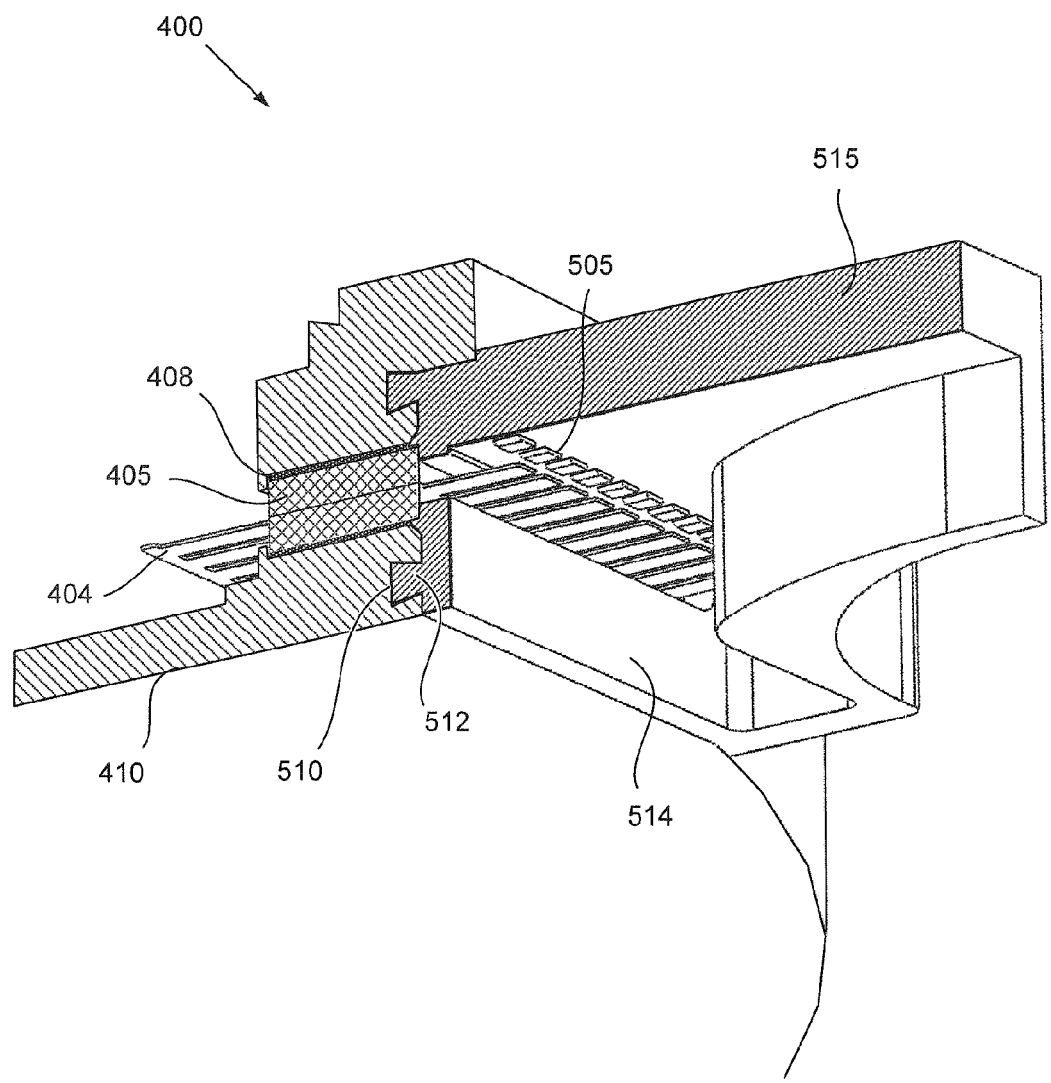
FIG. 5B is a cross sectional diagram of an illustrative hermetic case that includes a hermetic electrical feedthrough and polymeric header, according to one embodiment of principles described herein.
Figure 5C:
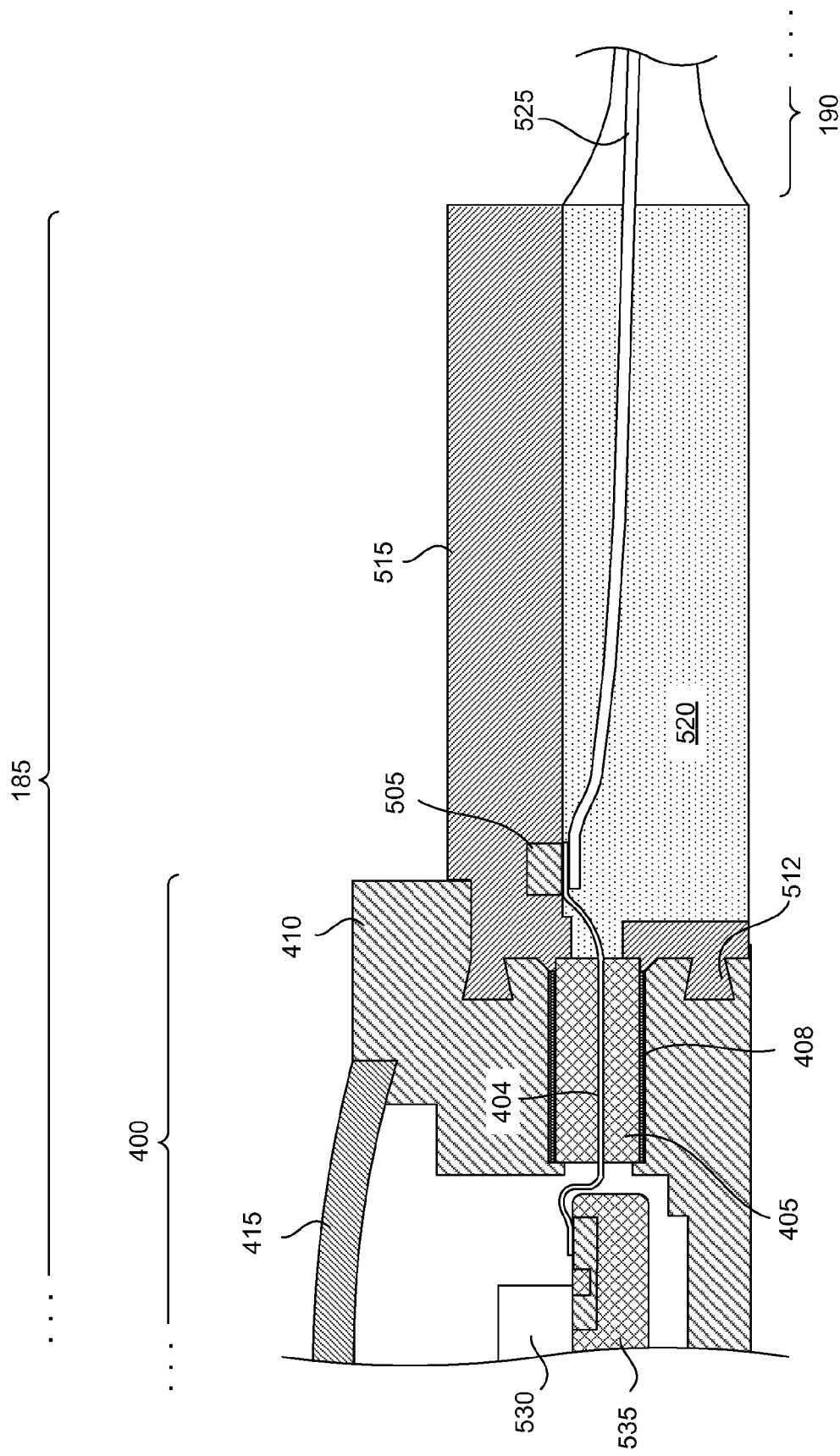
FIG. 5C is a cross sectional diagram of a portion of an illustrative internal processor, according to one embodiment of principles described herein.

FIG. 5B shows a partially cutaway perspective view of hermetic enclosure (400) that includes a polymeric header (515) and the imbedded interconnection contacts (505). The illustrative polymeric header (515) is attached to the case (410) with dovetails (512) that are configured to fit into the dovetail grooves (510). In this illustrative embodiment, the interconnection contacts (505) are in a linear array across the underside of the upper surface of the fan shaped cavity (514) in the polymeric header (515). The interconnection contacts (505) have the same number and spacing as the ribbon vias (404) that extend out of the ceramic body (405).

The polymeric header (515) may include a relatively thick upper surface and wall that form an internal cavity through which wires can pass from an external device to make electrical contact with the interconnection contacts (505) and/or the ribbon vias (404). The cavity (514) may have a variety of shapes, including the fan shape shown in FIG. 5B. The fan shape may have a number of advantages, including having a narrow end through which the cable can enter and a gradually broadening cross section that allows the wires to fan out to make contact with the ribbon vias (404) and interconnection contacts (505) that are spread across the wide end of the cavity (514). This fan shaped cavity (514) efficiently provides wire management and may be beneficial in providing strain relief for the cochlear lead wires.

According to one illustrative embodiment, the polymer header (515) can be formed using insert molding techniques. Insert molding includes various inserts in the injection mold. The polymeric material is injected into the mold and partially or wholly encapsulates the inserts. The inserts become an integral part of the injection molded part. In this illustrative embodiment, the case interconnection contacts (505) can be included in the mold as inserts and the polymeric header (515) can be injection molded around these parts. Additionally, the case (410) may also be included in the injection mold and become an integral part of the assembly.

According to one illustrative embodiment, the interconnection contacts (505) are included in the injection mold and are encapsulated on three sides by the polymeric material. However, the case (410) is not included in the injection mold. Instead, the dovetails (512) are formed by the mold. Following the molding of the polymeric header (515) and the integral interconnection contacts (505), additional steps can performed to prepare the polymeric header (515) for integration with case (410). For example, these steps may include quality checks, removal of flash, surface preparation, and precision cleaning. The dovetails (512) of the polymeric header (515) are then slid into the dovetail grooves (510). The dovetails (512) may be bonded in place using a variety of techniques, including ultrasonic, adhesive, epoxy, laser or other bonding techniques.

Additionally, a variety of other techniques could be used to form the polymeric header (515). For example, the polymeric header (515) could be machined from a solid piece of material and the interconnection contacts could be glued or otherwise fixed in place within the header (515). In another embodiment, the polymeric header (515) could be separately injection molded. The interconnection contacts (505) and case (410) could be later joined to the polymer header (515) using separate steps. Depending on the application, the polymeric header (515) can be formed from a variety of polymers, including polyether ether ketone (PEEK), polyethylene terephthalate (PET), polypropylene, polyurethane, silicone or other appropriate polymer.

The header (515) may have a variety of alignment and/or mechanical locking features. The use of dovetail grooves (510) and matching dovetails is only one illustrative example of a connection between the header (515) and the case (410). The header (515) and case (410) may have a variety of complementary geometries that provide a mechanically robust interconnection between the header (515) and the case (410). Male and female features may be on either the header or the implant case. For example, a post and hole system could be used. One or more posts or holes could be formed in the header (515) and one or more complementary holes or posts could be formed in the case (404). The header could then be interfaced with the case and the hole/post combinations could provide alignment, mechanical strength and increased surface area for bonding.

According to one alternative embodiment, the header (515) may be formed from titanium that has electrically isolated interconnection pads formed in the titanium. One illustrative technique for forming electrically isolated pads in a monolithic titanium body is described in U.S. App. Prov. App. No. 61/286,700, filed Dec. 15, 2009, entitled "Hermetic Electrical Feedthrough" to Kurt J. Koester which is incorporated herein by reference in its entirety. In this illustrative technique, a portion of the titanium is chemically or mechanically etched away to form one or more islands of titanium. The etched portion of the titanium is then filled with a dielectric such as titanium dioxide. After post processing, this produces electrically isolated pads that can serve as interconnection contacts. The titanium header can then be joined to the titanium case using laser welding and the ribbon vias attached to the interconnection contacts.

FIG. 5C shows a cross-sectional diagram of a portion of the internal processor (185). The internal processor (185) includes the hermetic enclosure (400). As described previously, the hermetic enclosure (400) includes a case top (415), a case (410), the hermetic electrical feedthrough (404, 405) and the polymeric header (515). According to one illustrative embodiment, the internal processor (185) includes internal electronics (530) that are supported and accessed by a circuit board (535). The portions of the ribbon via (404) that extend into the interior of the hermetic enclosure (400) connect to the circuit board (535).

The portions of the ribbon vias (404) that extend outward from the case (410) are connected to external devices by first being connected with the interconnection contacts (505). The ribbon vias (404) may be mechanically and/or electrically joined to the free surface of the interconnection contacts (505). For example, if the interconnection contacts (505) are formed from a dielectric material, the interconnection contacts (505) may only provide a mechanical connection that supports the ribbon vias (404). According to one illustrative embodiment, the interconnection contacts (505) are formed from platinum or a platinum alloy and form both an electrical and mechanical connection with the ribbon vias (404).

There are a number of advantages that result from continuous ribbon vias (404) passing through the ceramic body (405) and extending out of both sides of the ceramic body (405). A first advantage is that the interfaces between the ribbon vias (404) and other devices can be made remotely from the ceramic body (405). This preserves the integrity of the ceramic body (405) and isolates it from mechanical or thermal stresses associated with forming a mechanical or electrical connection.

A second advantage is that there is more flexibility in selecting the location where the connection between the ribbon vias (404) and the other devices is made. The ribbon vias (404) are flexible and can be moved to a desired location to make a contact. Because of this flexibility, some of the manufacturing tolerances of the header (515) and/or case (410) may be relaxed. Small errors in location can be compensated for by simply bending the ribbon to make the appropriate contact.

A third advantage is that no intermediate joining steps are required to connect the ribbon vias (404) to the internal circuit board (535). If the vias (404) ended at the surface of the ceramic body (405), a wire would have to be attached to the exposed surface of the ceramic body (405), routed to the appropriate location of the circuit board, and then connected to the circuit board. These additional wires, steps, and joints can be eliminated by having the ribbon vias (404) extend through the ceramic body (405) and attach directly to the circuit board (535). This may reduce the electrical resistance of connections between the internal electronics (530) and the exterior devices. By eliminating additional parts, joints, and steps, the implanted device may have a higher reliability and a lower cost.

The electrode wires (525) are connected to the ribbon vias (404) at the interconnection contacts (505). The interconnection contact (505) provides support and stability to the electrical junction. The interconnection contact (505) prevents tensile or other forces exerted by the electrode wire (525) from disturbing the ribbon via (404). As discussed previously, the polymer header (515) can be attached to the case (410) using the dovetail grooves (510, FIG. 5B) or other methods. The polymeric header (515) encapsulates the interconnection contacts (505) on three sides. The electrode wire (525) connects to one or more of the ribbon vias (404) and the interconnection contacts (505). In some embodiments where the interconnection contacts (505) are formed from a conductive material, it may be desirable for the electrode wires (525) to connect to a separate portion of the interconnection contact (505). In other embodiments, the electrode wires (525) may be joined directly to the ribbon vias (404). The ribbon vias (404) and the interconnection contacts (505) may be joined in a variety of ways including: TAB bonding, laser welding, soldering, brazing, or other techniques. The electrode wires (525) may be attached to the ribbon vias (404) using similar techniques. In this illustrative body, the electrode wires (525) proceed down a cochlear lead (190) to the electrode array (195, FIG. 3).

Following the attachment of the electrode wire (525) and the ribbon vias (404) to the interconnection contact (505), an encapsulant (520) may be placed inside the cavity of the polymeric header (515) to seal and protect the electrical wires and connections. According to one illustrative embodiment, the encapsulant (520) may be medical grade silicone. The encapsulant (520) may be deposited in a number of ways, including liquid injection molding or manual techniques.

Figure 5D:
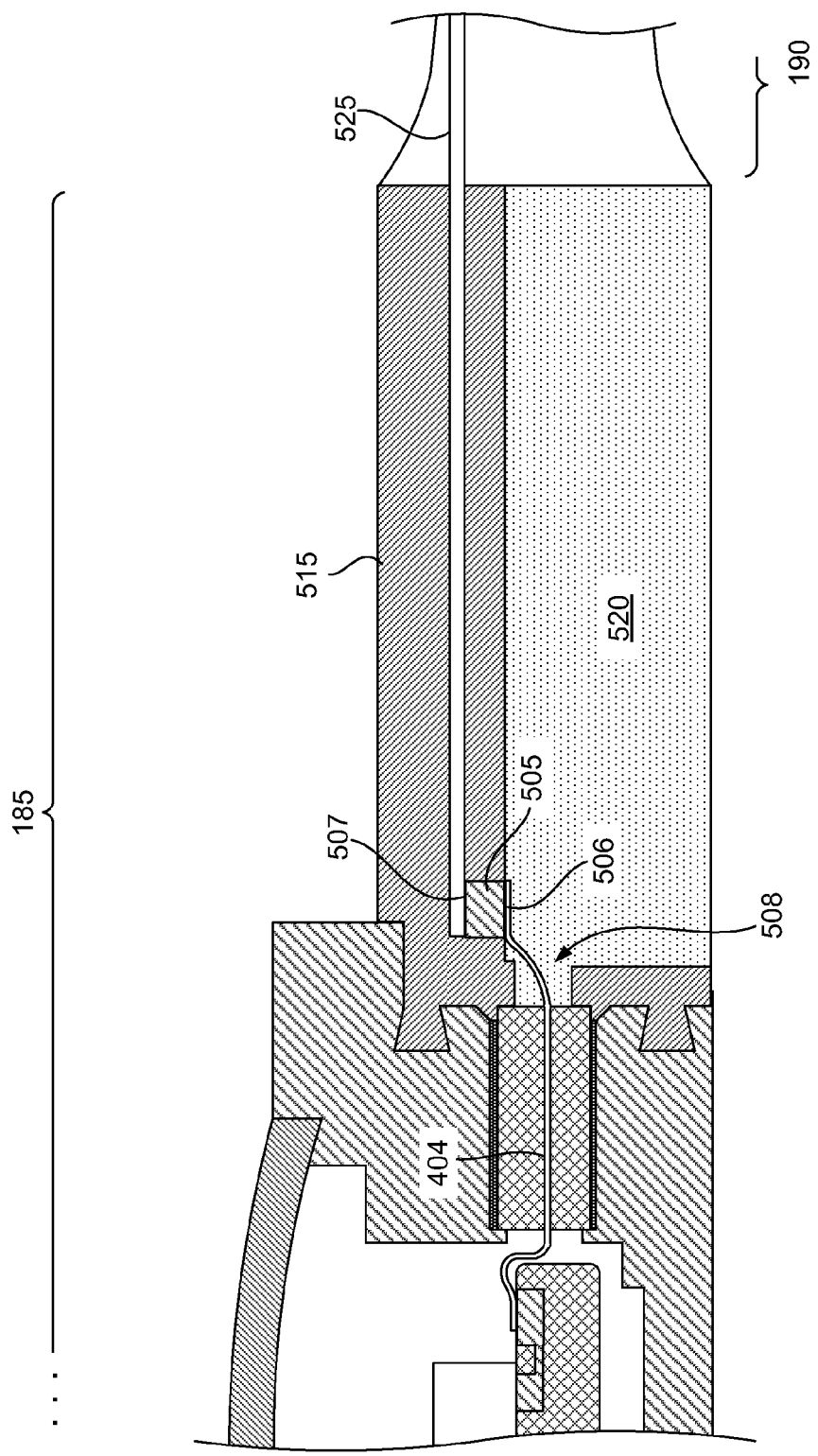
FIG. 5D is a cross sectional diagram of a portion of an illustrative internal processor, according to one embodiment of principles described herein.

FIG. 5D shows a cross-sectional diagram of a portion of the internal processor (185). As described above, the internal processor (185) includes the header (515). In this example, the electrode wires (525) and interconnection contacts (525) are formed directly into header (515). The ribbon vias (404) extend outward from the hermetic enclosure (400), through an aperture (508) in the header (515), and connect to the exposed surface (506) of the interconnection contacts (505). The electrode wires (525) connect to the interconnection contacts (525) on an opposite surface (507). In this embodiment, the electrode wires (525) may be connected to the opposite surface (507) of the interconnection contacts (525) prior to being insert molded into the header (515). This configuration may be particularly advantageous where the header (515) is formed from more compliant materials such as silicon rubber or cast urethane.

This configuration has the same advantages as described above with reference to the embodiment described in FIG. 5C. One additional advantage of this embodiment is that interfaces between the electrode wires (525) and the interconnection contacts (525) are formed and protected early in the manufacturing process. This can prevent damage to this interface during subsequent manufacturing steps.

Figure 6A:
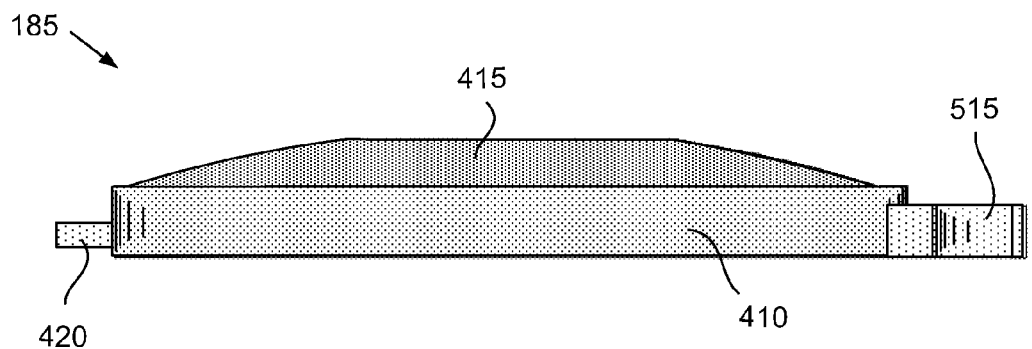
FIG. 6A is a side view of an illustrative internal processor, according to one embodiment of principles described herein.
Figure 6B:
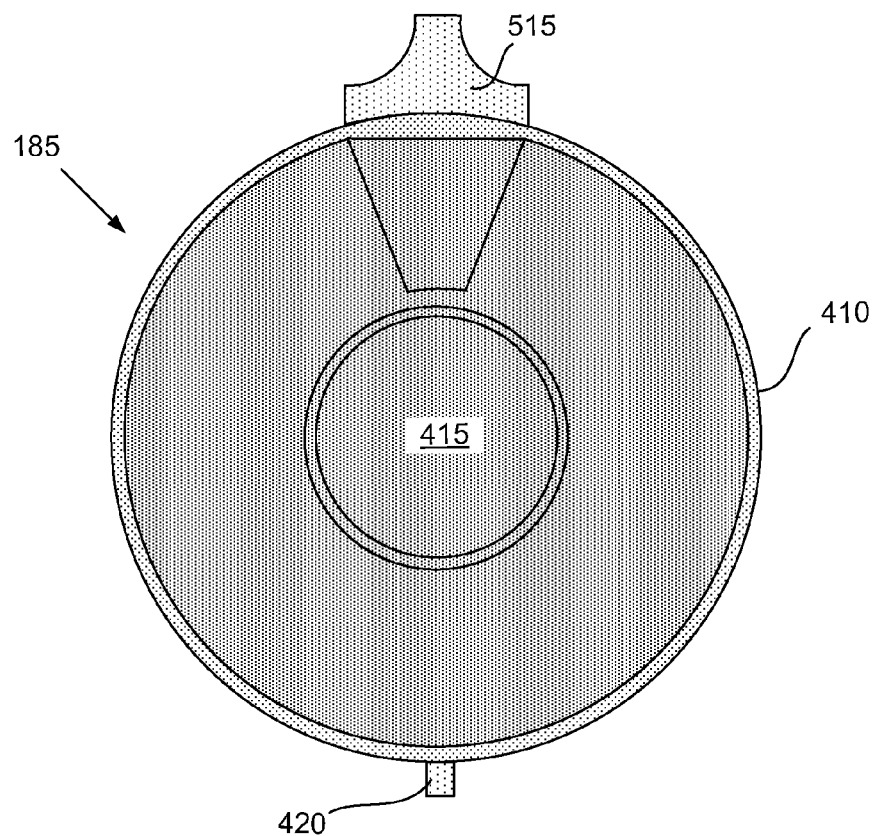
FIG. 6B is a top view of an illustrative internal processor, according to one embodiment of principles described herein.

FIG. 6A is a side view of an illustrative internal processor (185). The internal processor (185) includes the case (410), the case top (415), the polymer header (515), and various additional internal components. In some designs, a second hermetic feedthrough (420) may also be included. Although the geometry of the second hermetic feedthrough (420) is not discussed in detail, it could have similar components and be constructed in a similar fashion as the polymeric header (515) and the hermetic feedthrough (401, FIG. 4). FIG. 6B shows a top view of the internal processor (185) with the same components, including the polymeric header (515), the case (410), the case top (415), and the second hermetic feedthrough (420).

Figure 7:
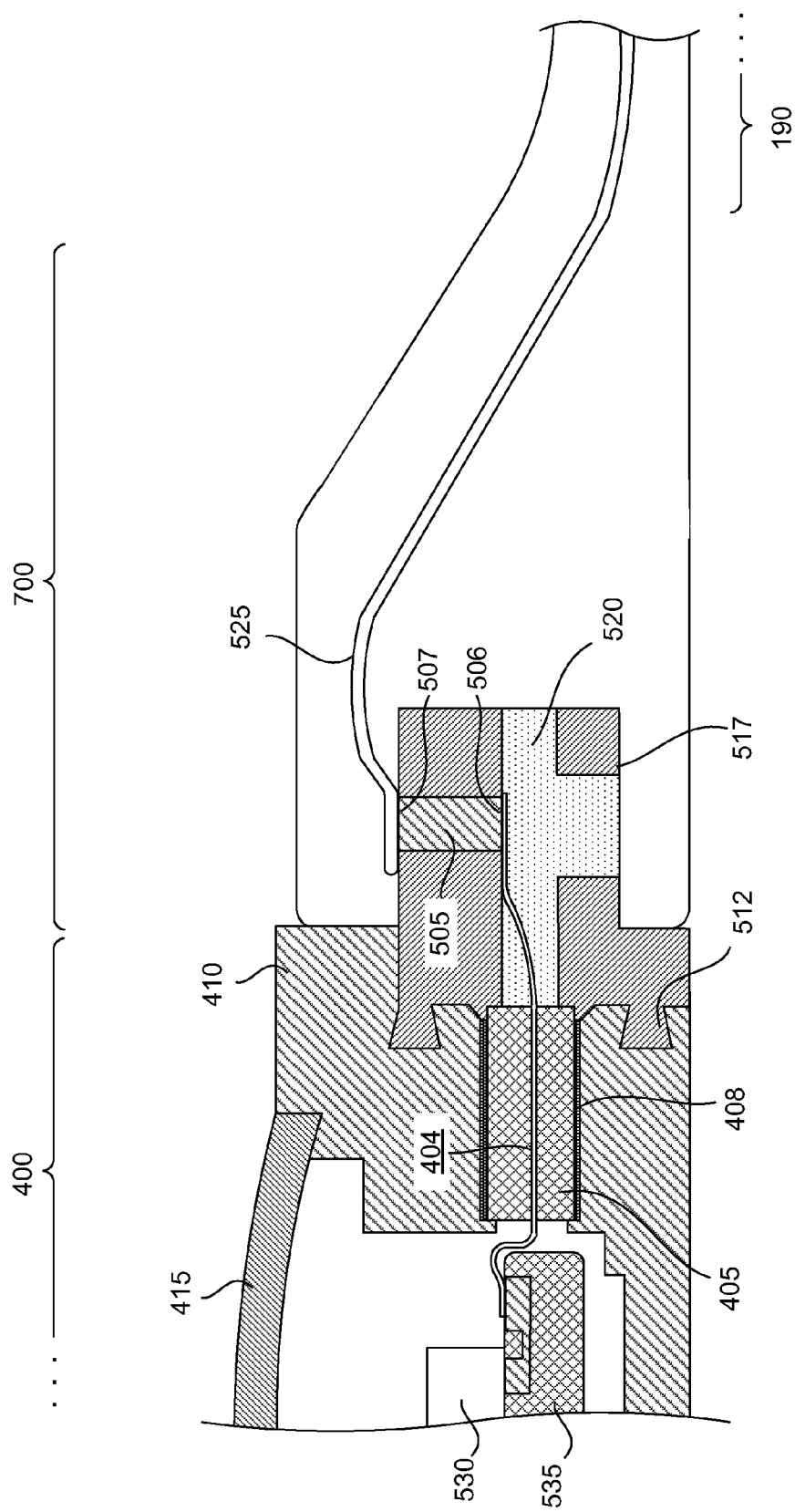
FIG. 7 is a cross sectional view of a hermetic enclosure with connectorized attachment, according to one embodiment of principles described herein.

FIG. 7 is a cross sectional diagram of an illustrative header (517) that is configured to interface with a connector (700) on the end of the cochlear lead (190). In these embodiments, the header (517) may be configured to form a socket or protrusion that interfaces with the connector (700). The interconnection contacts (505) may be more complex and/or extend entirely through a wall of the header (517). For example, the interconnection contacts (505) may extend through a wall of the header (517), with the ribbon vias (404) connecting to one free surface (506) of the interconnection contacts (505) and the conductors in the mating connector (700) may contact an opposite surface (507) of the interconnection contacts (505).

The header design can have variety of shapes and features which facilitate interfacing with a connector. For example, the header (515) may have a variety of mechanical locking features which secure a connector to the header (515). The header (515) may include a number of male or female features which are adapted to interface with a connector.

Figure 8A:
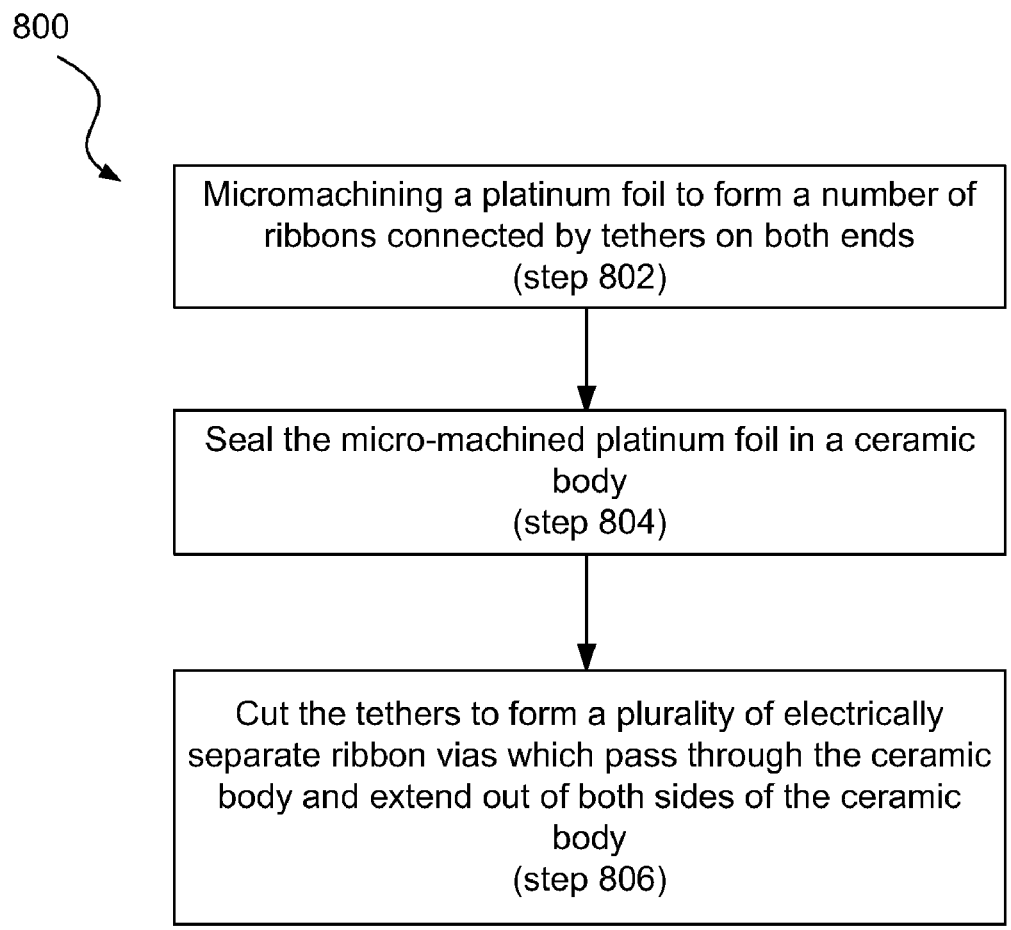
FIG. 8A is a flowchart that describes an illustrative method for forming a hermetic feedthrough with ribbon vias, according to one embodiment of principles described herein.

FIG. 8A shows one illustrative method (800) for forming an implantable hermetic feedthrough with ribbon vias. According to one illustrative embodiment, the hermetic feedthrough is formed by micro-machining a platinum foil to form a number of ribbons connected by tethers on both ends (step 802). The micro-machining may be performed using a number of technologies, including short pulse laser machining. The micro-machined platinum is then sealed in a ceramic body (step 804). For example, the micro-machined platinum may be placed between an upper and lower ceramic bodies which are then sintered under pressure. As described above, the sealing step may also include partially transient bonding between the platinum foil and the surrounding ceramic. The tethers can then be cut or removed to form a plurality of electrically separate ribbon vias which pass through the ceramic body and extend out of both sides of the ceramic body.

Figure 8B:
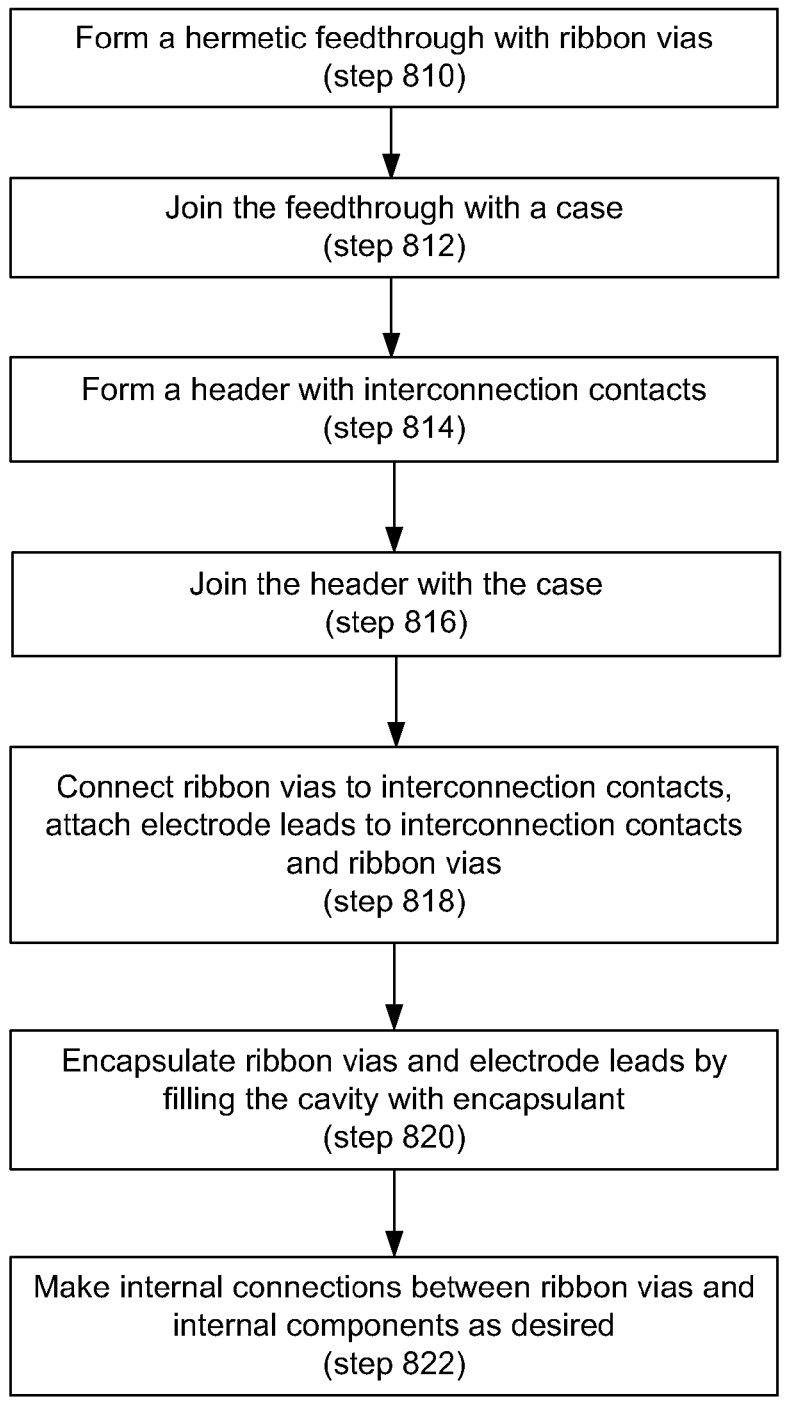
FIG. 8B is a flowchart that describes an illustrative method for making an attachment to an implantable hermetic feedthrough with ribbon vias, according to one embodiment of principles described herein.

FIG. 8B shows one illustrative method (808) for forming an attachment to an implantable hermetic feedthrough with ribbon vias. According to one illustrative embodiment, the hermetic feedthrough is formed with integral ribbon vias (step 810). One example of forming a hermetic feed through with ribbon vias is given in FIG. 8A. Next, the hermetic feedthrough can be joined with the case (step 812). For example, the case may be formed from titanium and include an aperture in its radial wall. As used in the specification and appended claims, the term "radial wall" refers to a generally curved perimeter wall which forms a closed shape. The radial wall need not be arcuate, and may have flat portions. The hermetic feedthrough can be brazed into the aperture using a gold or gold alloy braze material.

The polymeric header is formed with the interconnection contacts embedded in place (step 814). The polymeric header is joined to the case (step 816). As discussed above, the polymeric header may be insert molded, injection molded, and joined in a variety of ways to the case. The ribbon vias are then connected to the interconnection contacts and the electrode leads are connected to the interconnection contacts and ribbon vias (step 818). The cavity in the polymeric header may then be filled with encapsulant which surrounds at least a portion of the ribbon vias and the electrode leads (step 820). A variety of materials may be used to encapsulate the ribbon vias and electrode wires. By way of example and not limitation, medical grade silicone rubber may be used as the encapsulant material.

The internal connections between the ribbon vias and the electrical components within the hermetic enclosure can be formed (step 822). According to one illustrative embodiment, the ribbon vias may be TAB bonded to portions of the internal circuit board.

The illustrative method described above is only one embodiment of a method for forming an attachment with an implantable hermetic feedthrough. The steps may be performed in an alternative order, additional steps may be added, and steps may be combined. For example, where insert molding is used, the step of forming a header with interconnection contacts (step 814) may be combined with the step of joining the header with the case (step 816). Both the case and the interconnection contacts can be included in the mold. When the polymer is injected into the mold the header is simultaneously formed and joined to the case. An example of interchanging the order of the steps may be making internal connections with the ribbon vias (step 822) prior to forming external connections between the ribbon vias and interconnection pads (step 818).

Figure 9:
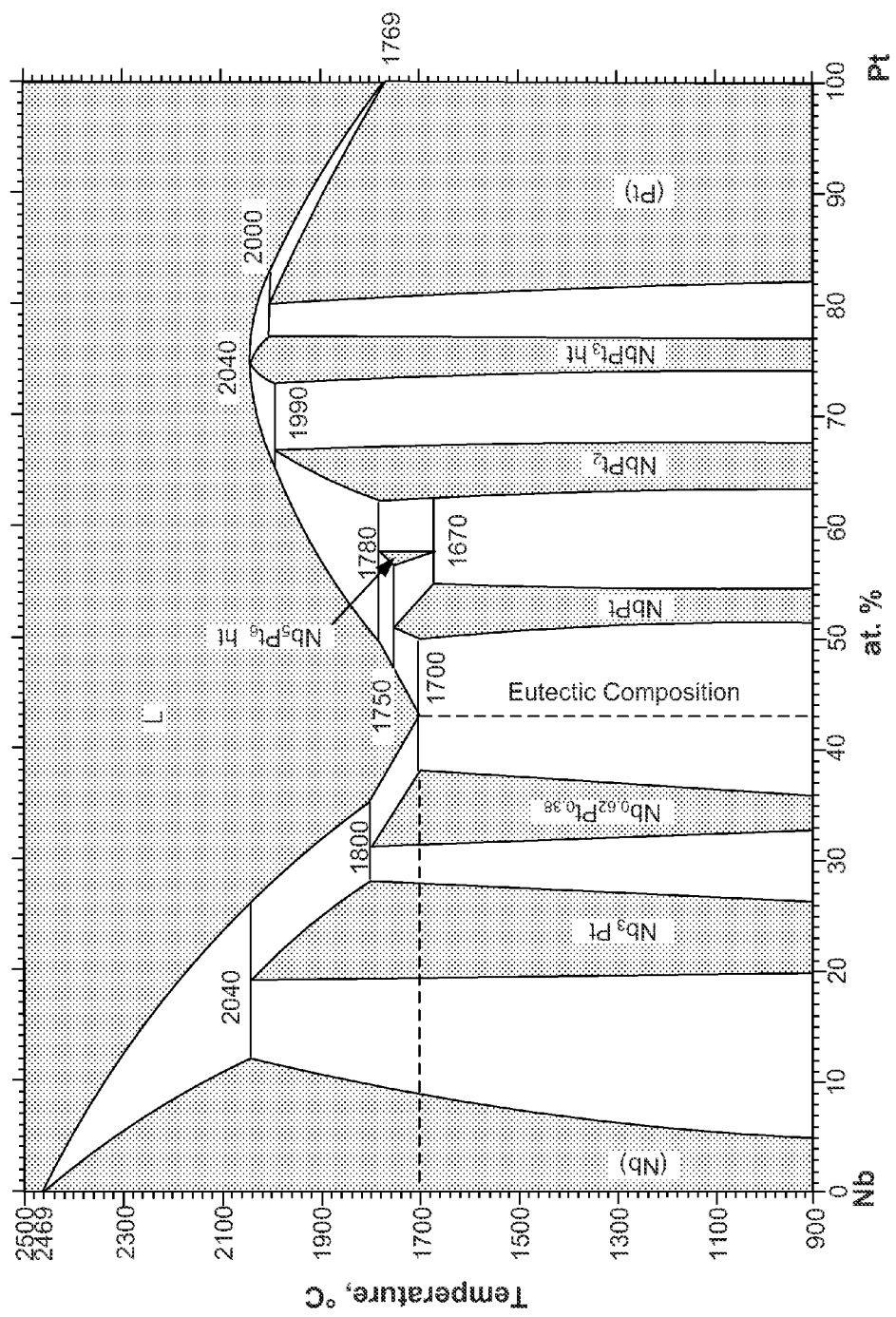
FIG. 9 is an illustrative binary phase diagram for niobium and platinum, according to one embodiment of principles described herein.

FIG. 9 is an illustrative binary phase diagram for niobium and platinum. The diagram in FIG. 9 will be referred to during the later discussion of partial transient liquid phase bonding in the hermetic electrical feedthroughs. The horizontal axis of the chart represents the composition, with a metal that is 100% niobium and 0% platinum being represented on the left and a metal that is 0% niobium and 100% platinum being represented on the right. The other various compositions are listed along the horizontal axis as the percent of platinum in the composition, with the balance being niobium. Various intermetallic compounds are shown as shaded areas with the associated name of the specific compound. The uppermost region, labeled with an "L" represents the temperatures at which specific niobium/platinum alloys are in a liquid state.

The eutectic composition is the specific ratio of the two metals that has a melting point that is lower than any other composition of the two metals. In this illustrative embodiment, the eutectic composition is approximately 43% niobium and 57% platinum. The eutectic temperature is approximately 1700° C., which is the lowest melting temperature of any niobium/platinum composition.

Another characteristic of the niobium/platinum alloy is the relatively high degree of solubility of niobium in platinum. This is shown by the shaded area to the bottom right of the chart labeled "(Pt)". For compositions with less than 18% niobium, the alloy is a solid solution of niobium in a platinum matrix. This leads to a homogenous composition for the range of platinum/niobium alloys with 18% niobium or less.

Figure 10A:
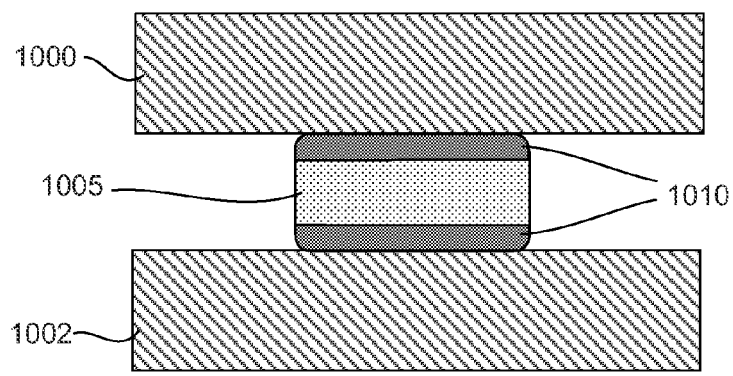
FIGS. 10A-10D are diagrams showing steps in an illustrative partial transient liquid phase bonding method which reduces the permeability of the hermetic feedthrough, according to one embodiment of principles described herein.

FIGS. 10A-10D are cross-sectional diagrams showing illustrative steps in manufacturing a hermetic electrical feedthrough using partial transient liquid phase bonding to decrease the permeability of the feedthrough. FIG. 10A shows a platinum ribbon (1005), which has its upper and lower surfaces coated with a niobium layer (1010). The niobium layers may be deposited in a number of ways and may be deposited on one or more of the surfaces of the ribbon (1005). For example, the niobium (1010) may be deposited using chemical vapor deposition on both surfaces of the platinum foil prior to micro-machining the foil into ribbons (1005). In other embodiments, the niobium (1010) may be deposited after the micro-machining of the platinum foil and may cover the entire perimeter of the ribbons (1005). In this embodiment, the niobium layer (1010) is substantially pure niobium. However, the niobium layer (1010) may be formed from a variety of niobium/platinum alloys which have a niobium composition that is greater than or equal to that of the eutectic composition.

Figure 10B:
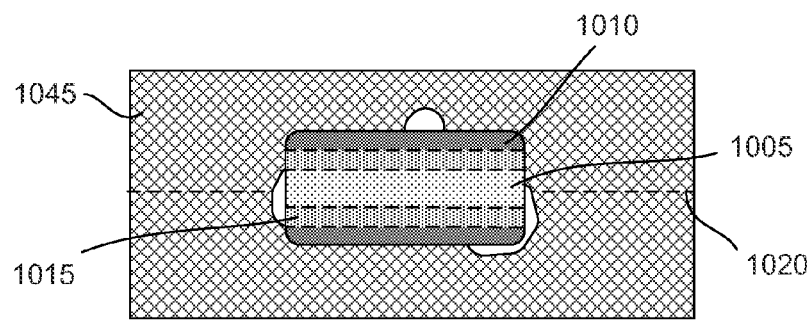

The platinum ribbon (1005) is sandwiched between an upper green ceramic tape (1000) and a lower green ceramic tape (1002). The assembly is then pressed together and sintered at an elevated temperature. This results in the densification and sintering of the green ceramic tapes (1000, 1002). FIG. 10B shows the platinum ribbon (1005) inside the densified ceramic body (1045), which is formed from the green ceramic tapes (1000, 1002; FIG. 10A.). According to one illustrative embodiment, the green ceramic tapes (1000, 1002; FIG. 10A.) are formed primarily of alumina with organic binders. During sintering, the temperature of the assembly is raised to approximately 1650 to 1700° C. while mechanical pressure is applied to the assembly. The organic binders are burned out of the two green ceramic tapes (1000, 1002; FIG. 10A) and the ceramic tapes are fused to form a boundary-less dielectric joint (1020). This forms a monolithic densified ceramic body (1045). During sintering, the niobium diffuses from the niobium layers (1010) into the platinum ribbon (1005) to form a diffusion zone (1015), which has a range of niobium/platinum compositions, including at least a portion that is at the eutectic composition.

In a next step, the process temperature is raised to at least the eutectic temperature. For example, when a niobium/platinum composition is used, the process temperature may be raised to between 1700 and 1750° C. At this temperature, the portion of the diffusion zone (1015) that is at the eutectic composition liquefies. As this portion liquefies, additional niobium and platinum diffuse into the liquid and the liquid portion grows to form a transient liquid phase which flows into voids surrounding the ribbon (1005).

Figure 10C:
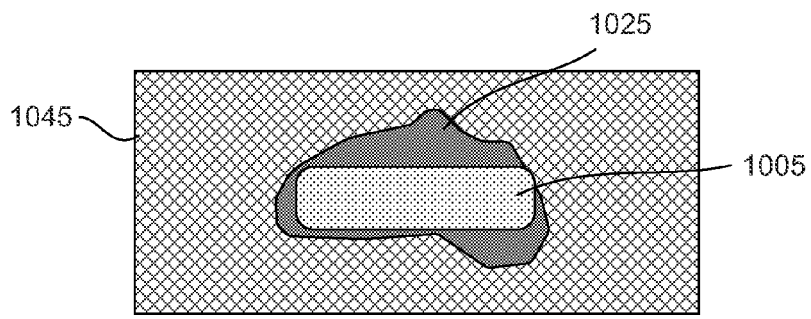

FIG. 10C shows the transient liquid (1025) flowing into the asperities surrounding the platinum ribbon (1005) and forming a bond between the ceramic body (1005) and the platinum ribbon (1005). The center portion of the platinum ribbon (1005) remains solid. At the eutectic temperature, niobium continues to diffuse out of the transient liquid (1025) and into the platinum ribbon (1005). This changes the composition of the transient liquid (1025) away from the eutectic composition (to the right on the phase diagram in FIG. 9). Consequently, the transient liquid (1025) solidifies after briefly being liquid. The transient liquid phase may provide a number of benefits, including wetting the alumina, a reaction bond between with the ceramic, filling in asperities, relieving stresses that may be present in the assembly, and other benefits.

Figure 10D:
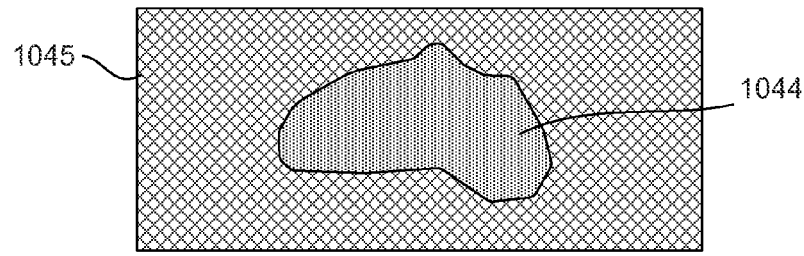

FIG. 10D shows one illustrative embodiment in which the niobium has uniformly diffused into the platinum ribbon to form a solid solution of niobium within the platinum. This results in a substantially uniform alloy composition through the cross-section of the ribbon via (1044). As discussed above the solid solubility limit of niobium in platinum is approximately 18% niobium. Consequently, to achieve a substantially uniform solid solution of niobium in platinum the overall ratio of niobium to platinum is less than or equal to approximately 18% niobium. This alloy (1044) forms a conductive path through ceramic body (1045) with reduced permeability.

Figure 11:
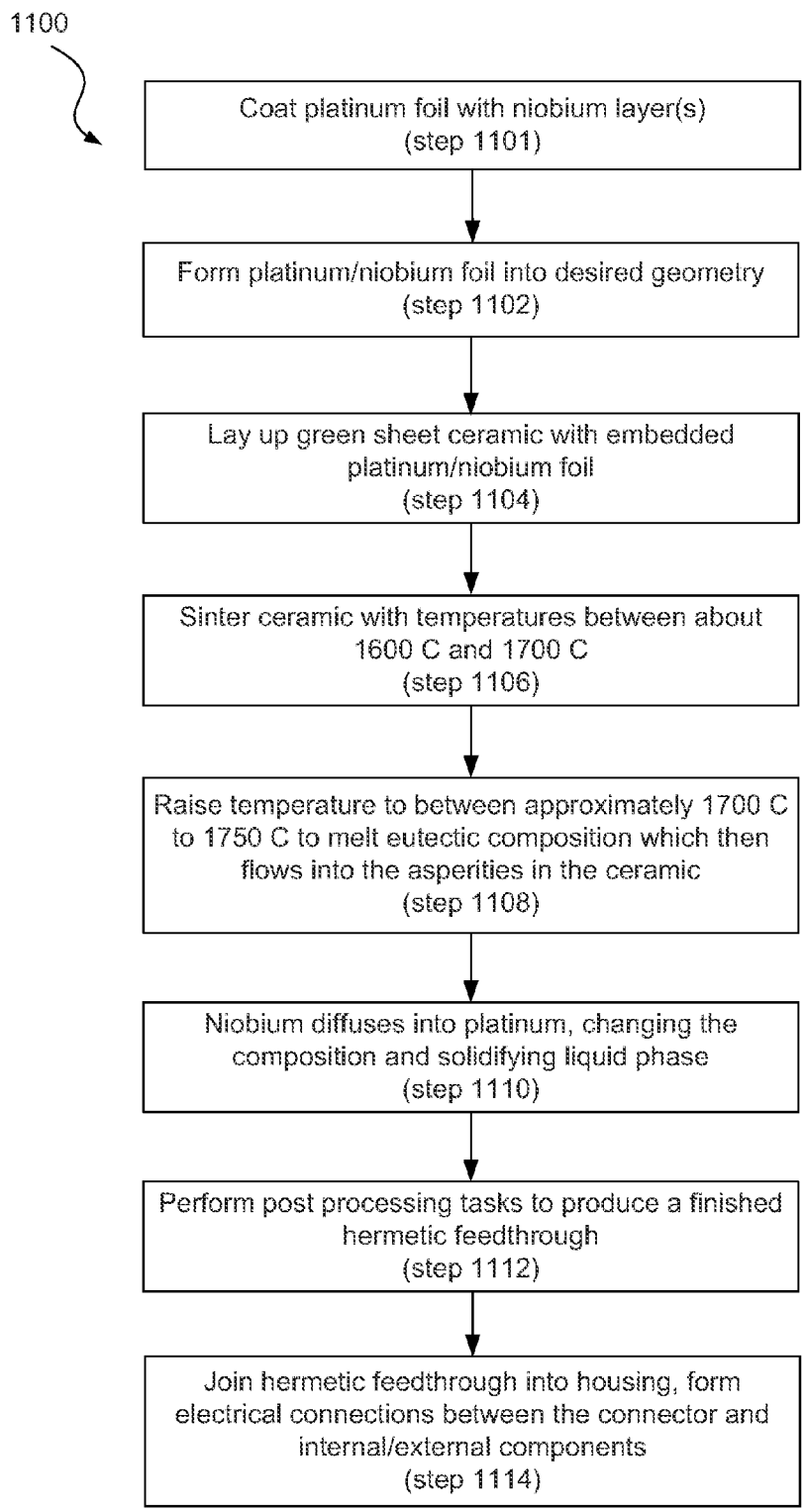
FIG. 11 is a flowchart showing an illustrative method for manufacturing a hermetic feedthrough using partial transient liquid phase bonding, according to one embodiment of principles described herein.

FIG. 11 is a flowchart showing an illustrative method for manufacturing a hermetic feedthrough using partial transient liquid phase bonding. The steps described below can be altered in sequence or replaced by alternative steps. In a first step, a sheet of platinum foil is coated with one or more niobium layers (step 1101). According to one illustrative embodiment, the sheet may be large enough to form a plurality of frames. The niobium layer could be patterned such that niobium is deposited over only a portion of the sheet. Alternatively, a niobium layer can be formed using niobium foil that is joined to the platinum foil. The platinum foil and niobium layer are formed into a frame having the desired geometry (step 1102). As discussed above, the platinum foil may have a variety of geometries, including a plurality of ribbons connected by tethers. Where a large sheet of platinum foil is used, a micro-machining process may be used to create cutouts into the platinum foil to form ribbons connected by tethers. The large sheet may then be segmented into a plurality of frames. As discussed above, each frame may comprise a plurality of ribbons connected tethers.

The platinum/niobium frame is then sandwiched between green ceramic tapes (step 1104). This assembly is then sintered under pressure and at temperatures between about 1600 to 1700° C. (step 1106). This step in the process is called "inclusion sintering" because the conductor is included in the ceramic during sintering. During inclusion sintering there are a number of factors that can be considered, including the shrinkage of the ceramic, burn out of organic binders, flow of ceramic material under pressure, the relative bonding that takes place between the embedded conductor and the surrounding ceramic, and other considerations. The considerations can influence various processing parameters, such as the process temperature, the geometry of the individual components within the assembly, the type of atmosphere (inert, vacuum, or reactive) in which the sintering takes place, and other parameters.

The process temperature is then raised to between approximately 1700 to 1750° C. to melt the eutectic composition which then flows into asperities and forms a bond with the surrounding ceramic (step 1108). These asperities may include grain boundaries between ceramic regions, voids between the ribbon via and the ceramic, and other discontinuities.

At this elevated temperature, the niobium diffuses into platinum, which changes the composition and solidifies the liquid phase (step 1110). A number of post processing tasks may be performed to produce a finished hermetic feedthrough (step 1112). For example, the post processing tasks may include the removal of the tethers to separate the frame into individual ribbons. The hermetic connector is then joined into the case and electrical connections between the hermetic connectors and internal/external components (step 1114). The hermetic feedthrough may be joined to the case in a variety of ways, including brazing, active metal brazing, ceramic/glass/metal bonding, transient liquid phase bonding, or other techniques. In some embodiments, the hermetic feedthroughs may be joined to a separate flange that is then laser welded to the titanium case.

In sum, the illustrative system and method for making attachments to implantable hermetic feedthroughs can decrease the manufacturing cost, increase the reliability of the device, decrease the electrical resistance between internal and external devices and protect the connections from failure.

The preceding description has been presented only to illustrate and describe embodiments and examples of the principles described. This description is not intended to be exhaustive or to limit these principles to any precise form disclosed. Many modifications and variations are possible in light of the above teaching.

What is claimed is:

1. An implantable hermetic system comprising:
   a hermetic case;
   a hermetic feedthrough sealed into an aperture in the case, the hermetic feedthrough comprising ribbon vias which form electrically conductive paths through a ceramic body, in which the ribbon vias extend out of both sides of the ceramic body; and
   a header comprising integral interconnection contacts, the header being attached to the case;
   in which the ribbon vias are directly attached to the interconnection contacts.

2. The system of claim 1, further comprising external wires connected to an external device; the external wires also being bonded to the interconnection contacts such that an electrical connection exists between the external wires and the ribbon vias.

3. The system of claim 1, further comprising an encapsulant which fills a cavity in the header and surrounds at least a portion of the ribbon vias.

4. The system of claim 3, in which the header and encapsulant are formed from polymeric materials.

5. The system of claim 4, in which the header is an insert molded polymer header.

6. The system of claim 1, in which the header is machined from a monolithic piece of bio-compatible material.

7. The system of claim 1, in which the interconnection contacts have substantially the same number and spacing as the ribbon vias.

8. The system of claim 1, in which the header comprises a cavity, the interconnection contacts being disposed in a wall of the cavity with at least one surface of each interconnection contact being exposed.

9. The system of claim 8, in which the header further comprises an aperture in a perimeter wall of the cavity, the ribbon vias entering the cavity through the aperture and being joined to the exposed surface of the interconnection contacts disposed in the wall of the cavity.

10. The system of claim 9, further comprising external wires exiting a cable and entering the cavity and fanning out to be joined with the interconnection contacts.

11. The system of claim 8, in which the cavity is a fan shaped cavity.

12. The system of claim 1, further comprising a first interface feature in the case, the header having a second complementary interface feature, the first interface feature and second complementary interface feature being coupled to mechanically join the case and the header.

13. The system of claim 1, in which attachment between the header and the case comprises an insert molded attachment.

14. The system of claim 1, in which attachment between the header and the case comprises an adhesive attachment.

15. The system of claim 1, in which the header and the integral interconnection contacts are formed from a monolithic piece of titanium, in which portions of titanium forming the integral interconnection contacts are electrically isolated by a dielectric from portions of the titanium that form the header.

16. The system of claim 15, in which the dielectric comprises titanium dioxide.

17. The system of claim 15, in which the hermetic case comprises titanium, in which the header is joined to the case using laser welding.

18. The system of claim 1, in which the integral interconnection contacts pass through a wall of the header and comprise a first exposed surface on a first side of the wall and a second exposed surface on a second side of the wall, in which a ribbon via is directly attached to the first exposed surface and a conductor to an external device is connected to the second exposed surface.

19. An implantable hermetic feedthrough comprising ribbon vias extending through a ceramic body, the hermetic feedthrough, being sealed into an aperture in a hermetic case, wherein the ribbon vias comprise a platinum foil coated with niobium such at when the ceramic body and plurality of ribbon vias are heated above a eutectic point, interfaces between the plurality of ribbon vias and the ceramic body are sealed using partially transient liquid phase bonding such that voids surrounding the plurality of ribbon vias are filled by a solid solution of platinum and niobium.

20. The feedthrough of claim 19, in which the ribbon vias are mechanically attached to interconnection contacts in a header, the header being attached to the hermetic case.

21. A method for forming an attachment to an implantable hermetic feedthrough with ribbon vias comprises:
   forming a hermetic feedthrough with ribbon vias;
   joining the hermetic feedthrough into an aperture in a case;
   forming a header with embedded interconnection contacts in a wall of the header;
   joining the header directly to the case;
   connecting a first end of the ribbon vias to the interconnection contacts;
   connecting wires from an external device to interconnection contacts; and
   encapsulating the ribbon vias and external wires.

22. An implantable medical device comprising:
   a titanium case having an aperture in a radial wall;
   a hermetic electrical feedthrough brazed into the aperture in the radial wall, the hermetic electrical feedthrough comprising:
      a ceramic body;
      a plurality of ribbon vias extending through the ceramic body, the plurality of ribbon vias comprising a micromachined platinum foil having a thickness of less than 50 microns and coated with niobium such that when the ceramic body and plurality of ribbon vias are heated above a eutectic point, interfaces between the plurality of ribbon vias and the ceramic body are sealed using partially transient liquid phase bonding such that voids surrounding the plurality of ribbon vias are filled by a solid solution of platinum and niobium;
   a header attached to the titanium case and encircling the hermetic feedthrough, the hermetic feedthrough having a fan shaped cavity and having integral interconnection contacts on the interior of the fan shape cavity, in which the ribbon vias are mechanically and electrically attached to the interconnection contacts;
   external wires passing through the fan shaped cavity and making electrical contact with the plurality of ribbon vias; and
   an encapsulant filling the fan shaped cavity and surrounding at least a portion of each ribbon via and each external wire.

23. An implantable hermetic feedthrough comprising ribbon vias extending out of a ceramic body, the hermetic feedthrough being sealed into an aperture in a hermetic case, in which the ribbon vias comprise a micromachined platinum foil having a thickness of less than 50 microns and coated with niobium such that when the ceramic body and plurality of ribbon vias are heated above a eutectic point, interfaces between the plurality of ribbon vias and the ceramic body are sealed using partially transient liquid phase bonding such that voids surrounding the plurality of ribbon vias are filled by a solid solution of platinum and niobium, and the center portions of the ribbon vias comprise tower amounts of niobium than the solid solution filling the voids.

24. A method for forming an attachment to an implantable hermetic feedthrough with ribbon vias comprises:
   forming a hermetic feedthrough with ribbon vias by:
      micromachining a platinum foil to form a number of ribbons connected by tethers on both ends;
      depositing a coating of niobium on the foil:
      sandwiching the foil between two ceramic bodies;
      heating the two ceramic bodies and platinum foil to a first temperature to form a diffusion zone between the coating of niobium and the platinum foil such that at least a portion of the diffusion zone comprises a eutectic composition of platinum and niobium and the two ceramic bodies are joined into a monolithic ceramic body;
      heating the ceramic bodies and platinum foil to a second higher temperature such that the eutectic composition of platinum and niobium liquefies and flows into voids surrounding the ribbon vias, in which at least a portion of the platinum foil embedded in the monolithic ceramic body remains solid during liquefaction of the eutectic composition;
      maintaining the second temperature such that diffusion of niobium into the solid platinum portion of the ribbon vias creates a hypereutectic composition of platinum and niobium within the voids surrounding the ribbon vias, the hypereutectic composition solidifying in the voids surrounding the ribbon vias; and
      cutting the tethers to form a plurality of electrically separate ribbon vias which pass through the ceramic body and extend out of both sides of the monolithic ceramic body;
   joining the hermetic feedthrough into an aperture in a case;
   forming a header with embedded interconnection contacts;
   joining the header with the case;
   connecting a first end of the ribbon vias to the interconnection contacts;
   connecting wires from an external device to interconnection contacts; and
   encapsulating the ribbon vias and external wires.

* * * * *